(12) United States Patent  
Schaus et al.

(10) Patent No.: US 9,095,393 B2  
(45) Date of Patent: Aug. 4, 2015

(54) METHOD FOR BALLOON-AIDED VERTEBRAL AUGMENTATION

(71) Applicants: Erin L. Schaus, Elk Grove Village, IL (US); John A. Krueger, Muskego, WI (US); Evan D. Linderman, Deerfield, IL (US)

(72) Inventors: Erin L. Schaus, Elk Grove Village, IL (US); John A. Krueger, Muskego, WI (US); Evan D. Linderman, Deerfield, IL (US)

(73) Assignee: CareFusion 2200, Inc., San Diego, CA (US)

(*) Notice: Subject to any disclaimer, the term of this patent is extended or adjusted under 35 U.S.C. 154(b) by 0 days.

(21) Appl. No.: 14/050,017

(22) Filed: Oct. 9, 2013

(65) Prior Publication Data

US 2014/0046334 A1    Feb. 13, 2014

Related U.S. Application Data

(63) Continuation-in-part of application No. 13/483,919, filed on May 30, 2012, now Pat. No. 8,894,658.

(51) Int. Cl.
| | | |
|---|---|---|
| *A61F 2/46* | (2006.01) | |
| *A61B 17/88* | (2006.01) | |
| *A61B 17/16* | (2006.01) | |
| *A61B 17/00* | (2006.01) | |
| *A61B 19/00* | (2006.01) | |

(52) U.S. Cl.
CPC ......... *A61B 17/8822* (2013.01); *A61B 17/8805* (2013.01); *A61B 17/8855* (2013.01); *A61B 17/1642* (2013.01); *A61B 17/8811* (2013.01); *A61B 2017/00867* (2013.01); *A61B 2019/462* (2013.01); *A61B 2019/4857* (2013.01); *A61B 2019/5466* (2013.01)

(58) Field of Classification Search
CPC ........... A61B 17/8805; A61B 17/8811; A61B 17/885; A61B 17/8855; A61B 17/8852
USPC .................... 606/86 R, 92–94, 279
See application file for complete search history.

(56) References Cited

U.S. PATENT DOCUMENTS

| | | |
|---|---|---|
| 4,969,888 A | 11/1990 | Scholten et al. |
| 5,047,015 A | 9/1991 | Foote et al. |
| 5,091,205 A | 2/1992 | Fan |
| 5,108,404 A | 4/1992 | Scholten et al. |
| 5,201,753 A | 4/1993 | Lampropoulos et al. |
| 5,209,732 A | 5/1993 | Lampropoulos et al. |
| 5,827,289 A | 10/1998 | Reiley et al. |
| 5,849,014 A | 12/1998 | Mastrorio et al. |
| 5,972,015 A | 10/1999 | Scribner et al. |

(Continued)

OTHER PUBLICATIONS

International Search Report and Written Opinion of the International Searching Authority for International Application No. PCT/US2013/040975, dated Aug. 30, 2013, 14 pages.

*Primary Examiner* — Anu Ramana  
(74) *Attorney, Agent, or Firm* — Brinks Gilson & Lione

(57) ABSTRACT

An expandable member bone augmentation system and single-access-point methods for bone augmentation using same are provided. In certain embodiments, a pre-curved stylet with an overlying delivery tube may be used to target an approximately centered target site within a bone structure, facilitating direction thereto of an expandable member useful for creating a cavity that may receive curable material to restore bone height and/or to reinforce the bone structure. An expandable member such as, for example, a balloon can be used to create a plurality of voids by displacing bone material, where the voids can be filled with curable material to augment the bone.

20 Claims, 18 Drawing Sheets

(56) References Cited

U.S. PATENT DOCUMENTS

| | | |
|---|---|---|
| 6,066,154 A | 5/2000 | Reiley et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,423,083 B2 | 7/2002 | Reiley et al. |
| 6,605,056 B2 | 8/2003 | Eidenschink et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,632,235 B2 | 10/2003 | Weikel et al. |
| 6,641,587 B2 | 11/2003 | Scribner et al. |
| 6,663,647 B2 | 12/2003 | Reiley et al. |
| 6,716,216 B1 | 4/2004 | Boucher et al. |
| 6,726,691 B2 | 4/2004 | Osorio et al. |
| 6,852,095 B1 | 2/2005 | Ray |
| 6,899,719 B2 | 5/2005 | Reiley et al. |
| 6,923,813 B2 | 8/2005 | Phillips et al. |
| 6,979,341 B2 | 12/2005 | Scribner et al. |
| 6,981,981 B2 | 1/2006 | Reiley et al. |
| 7,044,954 B2 | 5/2006 | Reiley et al. |
| 7,153,306 B2 | 12/2006 | Ralph et al. |
| 7,156,861 B2 | 1/2007 | Scribner et al. |
| 7,166,121 B2 | 1/2007 | Reiley et al. |
| 7,241,303 B2 | 7/2007 | Reiss et al. |
| 7,252,671 B2 | 8/2007 | Scribner et al. |
| 7,252,672 B2 * | 8/2007 | Yetkinler et al. .................. 606/92 |
| 7,261,720 B2 | 8/2007 | Stevens et al. |
| 7,563,265 B1 | 7/2009 | Murphy |
| 7,713,273 B2 | 5/2010 | Krueger et al. |
| 7,799,035 B2 | 9/2010 | Krueger et al. |
| 7,922,690 B2 | 4/2011 | Plishka et al. |
| 8,128,633 B2 | 3/2012 | Linderman et al. |
| 8,226,657 B2 | 7/2012 | Linderman et al. |
| 2002/0026195 A1 | 2/2002 | Layne et al. |
| 2004/0167562 A1 | 8/2004 | Osorio et al. |
| 2006/0095064 A1 | 5/2006 | Scribner et al. |
| 2006/0235460 A1 | 10/2006 | Reiley et al. |
| 2006/0276819 A1 | 12/2006 | Osorio et al. |
| 2007/0010745 A1 | 1/2007 | Foot et al. |
| 2007/0021769 A1 | 1/2007 | Scribner et al. |
| 2007/0142842 A1 | 6/2007 | Krueger et al. |
| 2007/0198024 A1 | 8/2007 | Plishka et al. |
| 2008/0058823 A1 | 3/2008 | Reiley et al. |
| 2008/0140083 A1 | 6/2008 | Reiley et al. |
| 2009/0076517 A1 | 3/2009 | Reiley et al. |
| 2009/0088788 A1 | 4/2009 | Mouw |
| 2009/0131950 A1 | 5/2009 | Liu et al. |
| 2009/0204120 A1 | 8/2009 | Trosken et al. |
| 2010/0087828 A1 | 4/2010 | Krueger et al. |
| 2011/0046737 A1 | 2/2011 | Teisen |
| 2011/0112507 A1 | 5/2011 | Linderman et al. |
| 2011/0112588 A1 | 5/2011 | Linderman et al. |
| 2012/0016371 A1 | 1/2012 | O'Halloran et al. |
| 2012/0239047 A1 | 9/2012 | Linderman et al. |

\* cited by examiner

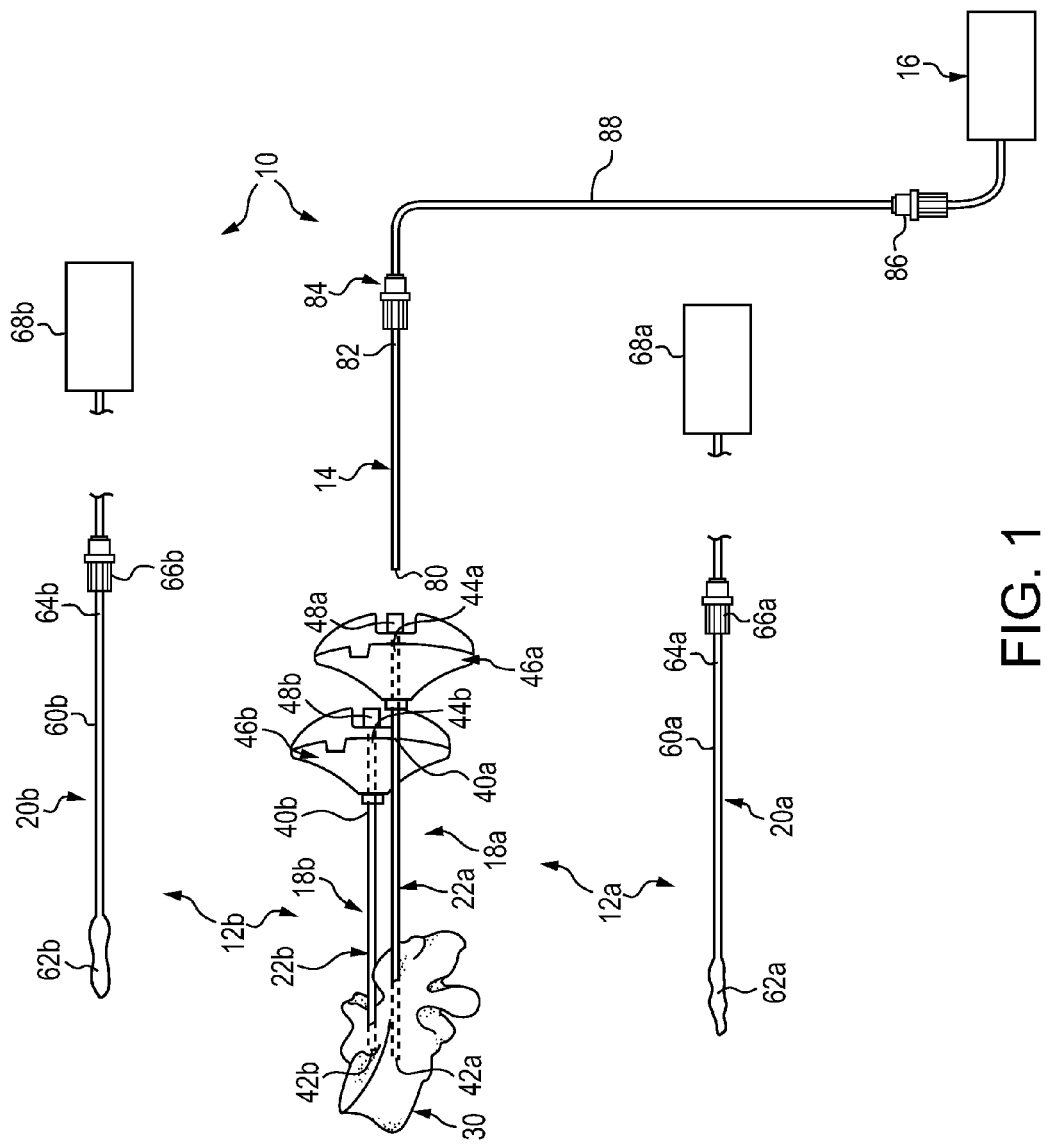

METHOD FOR BALLOON-AIDED VERTEBRAL AUGMENTATION

CROSS-REFERENCE TO RELATED APPLICATIONS

This application is a continuation-in-part of co-pending, co-owned U.S. patent application Ser. No. 13/483,919, filed May 30, 2012, which is incorporated by reference herein in its entirety.

TECHNICAL FIELD

Embodiments disclosed herein generally relate to methods for stabilizing bone structures. More particularly, they relate to systems and methods for stabilizing and restoring the height of a bone structure such as, for example, a vertebral body.

BACKGROUND

Surgical intervention of damaged or compromised bone sites has proven highly beneficial for patients, including, for example, patients with back pain associated with vertebral damage. The vertebral damage may be due to injury and/or a degenerative condition such as, for example, aging and/or osteoporosis. The damage associated with these conditions may also affect long bones, the pelvis, and other bones.

Bones of the human skeletal system include mineralized tissue that may be generally categorized into two morphological groups: "cortical" bone and "cancellous" bone. Outer walls of all bones are composed of cortical bone, which is a dense, compact bone structure characterized by a microscopic porosity. Cancellous or "trabecular" bone forms the interior structure of bones. Cancellous bone is composed of a lattice of interconnected slender rods and plates known by the term "trabeculae".

During certain bone-related procedures, cancellous bone is supplemented by an injection of a palliative (or curative) material employed to stabilize the trabeculae. For example, superior and inferior vertebrae in the spine may be beneficially stabilized by the injection of an appropriate, curable material (e.g., PMMA or other bone cement or bone curable material). In other procedures, percutaneous injection of stabilization material into vertebral compression factors, by, for example, transpedicular or parapedicular approaches, has proven beneficial in relieving pain and stabilizing damaged bone sites. Such techniques are commonly referred to as vertebroplasty.

A conventional vertebroplasty technique for delivering the bone stabilizing material entails placing a cannula with an internal trocar into the targeted delivery site, generally conducted in a bipedicular manner (i.e., via two pedicles of a vertebra). The cannula and trocar are used in conjunction to pierce the cutaneous layers of a patient above the hard tissue to be supplemented, then to penetrate the hard cortical bone of the vertebra, and finally to traverse into the softer, cancellous bone underlying the cortical bone. After the assembly is positioned in the cancellous bone, the trocar may be removed, leaving the cannula in the appropriate position for delivery of curable material that will reinforce and solidify the target site.

In some instances, an effectiveness of the procedure may be enhanced by forming a cavity or void within the cancellous bone, and then depositing the curable material in the cavity. For example, a balloon or other expandable device may be initially deployed and then expanded in a particular vertebroplasty procedure sometimes referred to as kyphoplasty. This action, in turn, compresses cancellous bone and other tissue to form a cavity, and may also cause a "height" of the bone to increase. As a point of reference, vertebroplasty is a common treatment for a fractured vertebral body, and the height of a fractured vertebral body is oftentimes significantly less than a native or natural height that existed before vertebral degeneration. It has been postulated that the height of a fractured vertebral body may be restored or elevated to a near-normal state when subjected to internal expansion via a balloon or other expandable member (e.g., a mechanically, hydraulically, and/or pneumatically expandable member configured to displace bone material, which may be embodied as a balloon, a bag that is mesh, porous, or generally non-porous, a basket, or any other medically appropriate structure). The mechanics of height restoration in conjunction with vertebroplasty stabilization is currently unclear at best. For example, certain techniques may employ a bipedicular approach in which two balloons are inserted into the vertebral body and inflated, resulting in an increase in height (and the cavity or cavities described above).

There exists a need in the medical device field for improved systems and methods for restoring the height of, and stabilizing, a fractured vertebral body or other bone structure. In particular, it would be desirable to provide apparatus and methods to symmetrically provide bone augmentation that stabilizes a bone structure such as a vertebra, and that may also provide some height-restoration of said bone structure.

It may be desirable to provide a system and method that provides advantages with regard to reduced complexity and reduced procedure time while maintaining advantages of dual-balloon kyphoplasty and perhaps offering superior bone-centralization and symmetry of curable material placement, while offering a further advantage of a single surgical wound site rather than traditional bipedicular operations for vertebral procedures and other multi-puncture procedures for treatment of other bones.

BRIEF SUMMARY

In one aspect, embodiments disclosed herein may include a method of balloon-aided vertebroplasty, as well as methods for augmentation of other bones, using multiple inflations of a single balloon to facilitate the bone-augmentation. In certain embodiments, a pre-curved stylet may be used to target an approximately centered target site within a bone structure, facilitating direction thereto of an expandable member useful for creating a cavity that may receive curable material to restore bone height and/or to reinforce the bone structure. The expandable member may be constrained by an outer tube during certain method steps, and exposed therefrom for other method steps, during which the expandable member may be inflated to create one or more cavities.

BRIEF DESCRIPTION OF THE DRAWINGS

FIG. 1 is an exploded view of a curable material delivery and height restoration system, using apparatus for bipedicular access;

DETAILED DESCRIPTION

Figure 2A:
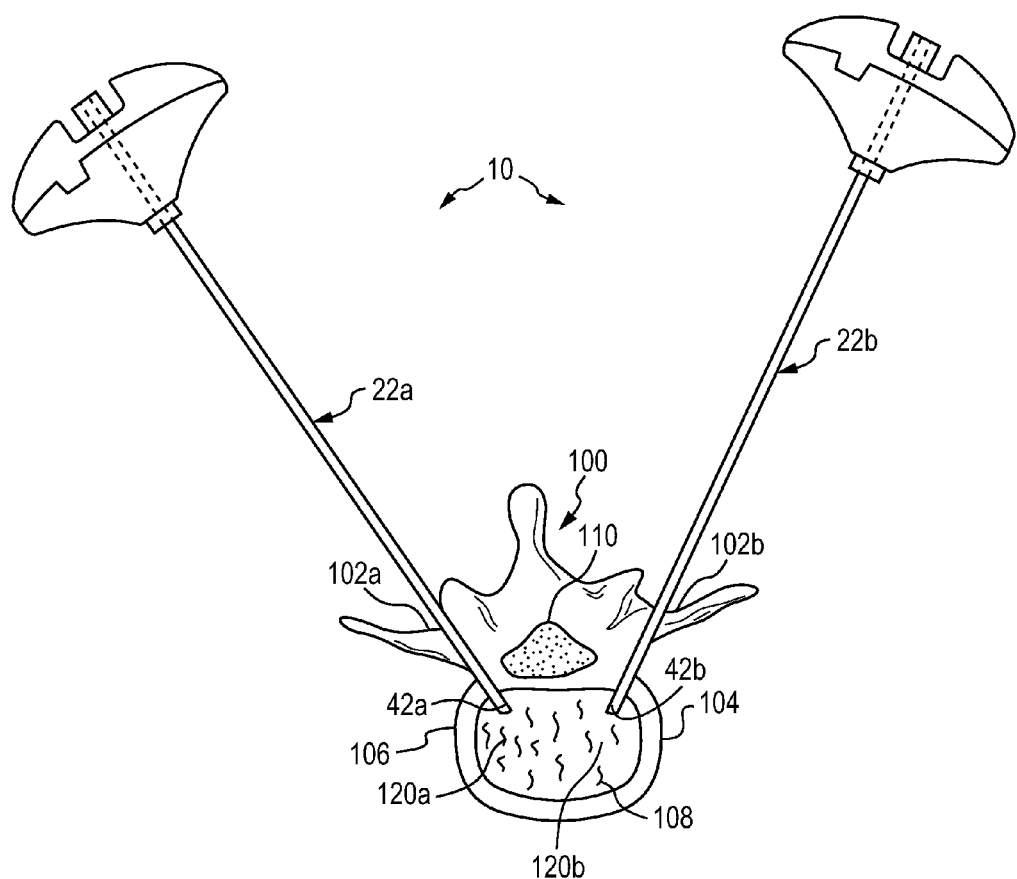
FIGS. 2A and 2B illustrate use of the system of FIG. 1 in performing a height restoration and curable material delivery procedure relative to a vertebra, with the vertebra being shown from a superior perspective.
Figure 2B:
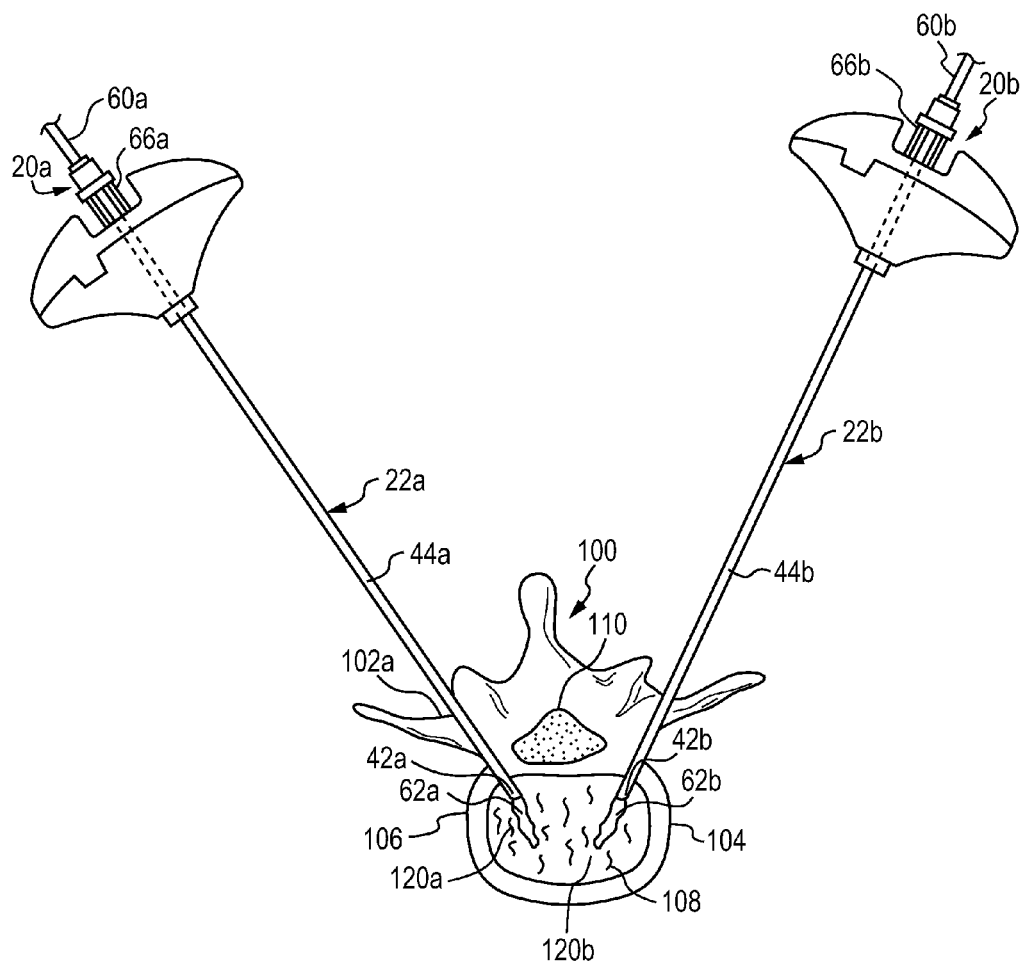

Embodiments are described with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Various embodiments will be described more fully hereinafter. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The word "alternatively" and its variants are used inclusively rather than exclusively (i.e., "X, alternatively, Y" means "X and/or Y" rather than "only X or only Y") unless otherwise apparent.

Currently, balloon assisted vertebral augmentation procedures are performed using a bipedicular approach, which allows internal cavities to be created on both sides of a single vertebral body. Cement is then injected into both halves of the vertebral body through each of the pedicles or through one pedicle using a curved needle system, such as, for example, an AVAflex® system (CareFusion Corp., San Diego, Calif.). The proposed method uses a device such as disclosed herein (with reference to FIGS. 4A-4F) to introduce a balloon, which can be inflated across the vertebral body midline (described below with reference to the method illustrated in FIGS. 5A-5D). It allows physicians to perform targeted balloon placement using the flexible, curved tip of the needle or stylet. It also reduces the need for doctors to perform bipedicular vertebral augmentation procedures on a single vertebral body. In a kyphoplasty procedure, it is often ideal to inflate a balloon through a single access point in a vertebral body to keep the procedure as minimally invasive as possible and minimize trauma to the pedicles. Knowing that vertebral bodies may be large compared to the balloon length, there may be advantages to using this device with the present method.

After inflating the balloon in a targeted area (which may be across/opposite the midline from the introducing/puncture site), the balloon may be retracted along the same pathway and re-inflated to create a larger cavity or two distinct cavities within a single vertebral body. This may be important because it mimics symmetric balloon inflation (cavity creation) in both halves of the vertebral body, as seen with the bipedicular approach shown in FIG. 3A, and it can also provide a larger cavity for cement containment. This concept is also valuable knowing that no two vertebral bodies are the same. Each will have a different geometry and fracture type. This concept provides the ability to position the balloon in distinct locations within the vertebral body through one access point. For example, a single path may allow the physician to stabilize both the upper and lower endplates. This method could stabilize a cleft fracture and then create a void in other location of the vertebral body. In addition to irregular bones, such as vertebral bodies, this method and tools may also be used to aid fracture repairs in other bones such as long bones and flat bones. Through a single access point, multiple voids may be created to fill fractures or facility screw or implant placement. Therefore, there exists the need to create a product that will safely create a targeted large cavity or multiple generally distinct cavities within bone using a single access point approach.

One embodiment of a curable material delivery and height restoration system 10 is shown in FIG. 1. The system 10 includes a first delivery assembly 12*a*, a second delivery assembly 12*b*, and at least one source of curable material 16. The delivery assemblies 12*a*, 12*b* may be substantially identical, and each includes a cannula device 18*a*, 18*b* and a cavity-forming device 20*a*, 20*b*. Details on the various components are provided below. In general terms, however, the cannula devices 18*a*, 18*b* each include an access cannula 22*a*, 22*b* for insertion into a bone site of interest in a patient. In the embodiment depicted in FIG. 1, the bone site of interest is a vertebra 30. After the access cannulas 22*a*, 22*b* are desirably located relative to the vertebra 30, a portion of each of the cavity-forming devices 20*a*, 20*b* are delivered to the vertebra 30 via the corresponding access cannula 22*a*, 22*b*, and operated to form cavities. The second cavity-forming device 20*b* (alternatively the first cavity-forming device 20*a*) may be removed, and the source of curable material 16 connected to the second cannula 22*b*. In this regard, a delivery tube 14 may be employed, extending from the source 16 and through the second cannula 22*b*.

Thereafter, the curable material source 16 is operated to deliver curable material to the cavity via the second cannula 22*b* and/or the delivery tube 14. Subsequently, the first cavity-forming device 20*a* may be removed and the curable material source 16 is connected to the first cannula 22*a* (for example, via the delivery tube 14). The curable material source 16 is operated to deliver curable material into the corresponding cavity. With the approaches disclosed herein, the systems and methods disclosed herein will be able to provide for restore a height of the vertebra (or other bone site) 30 to a normal or near-normal state, and the delivered curable material will provide desirable stabilization.

The system 10 may be used for a number of different procedures including, for example, vertebroplasty and other bone augmentation procedures in which curable material is delivered to a site within bone, as well as possibly to remove or aspirate material from a site within bone. The system 10 is highly useful for delivering a curable material in the form of a bone curable material. The phrase "curable material" within the context of the substance that may be delivered by the systems and methods described herein is intended to refer to materials (e.g., composites, polymers, and the like) that have a fluid or flowable state or phase and a hardened, solid or cured state or phase.

Curable materials may include, but are not limited to, injectable bone cements (such as polymethylmethacrylate (PMMA) bone curable material), which have a flowable state wherein they may be delivered (e.g., injected) by a cannula to a site and subsequently cure into hardened, cured material. Other materials such as calcium phosphates, bone in-growth materials, antibiotics, proteins, etc., may be used in place of, or to augment bone cement (but do not affect an overriding characteristic of the resultant formulation having a flowable state and a hardened, solid, or cured state). This would allow the body to reabsorb the curable material and/or improve the clinical outcome based on the type of filler implant material. Although FIG. 1 illustrates a single source of curable material 16, in other embodiments, two (or more) sources may be provided. The sources may contain identical curable material compositions; alternatively, the compositions may differ (e.g., a first source may contain bone cement, while a second source contains a mixture of bone cement and bone in-growth material).

As mentioned above, the cannula devices 18a, 18b may be substantially identical, and each includes the outer/access cannula 22a, 22b. The cannula 22a, 22b is provided to be positioned in (or immediately proximate) the target or injection site for delivery of the corresponding cavity-forming device 20a, 20b, as well as curable material. The cannula 22a, 22b preferably is made of a surgical grade of stainless steel, but may be made of known equivalent material(s) that are both biocompatible and substantially non-compliant at the expected operating pressures. The cannulas 22a, 22b each define a proximal region 40a, 40b, a distal end 42a, 42b, and a lumen 44a, 44b (referenced generally), respectively, to allow various equipment such as the cavity-forming device 20a, 20b, a delivery tube 14, one or more stylets (not shown here, but discussed and illustrated with reference to embodiments of FIGS. 4A-4H below), and/or other elements, to pass therethrough.

A handle 46a, 46b surrounds the proximal region 40a, 40b of the cannula 22a, 22b for manipulating the cannula 22a, 22b and for connecting the cannula 22a, 22b with one or more of the cavity-forming device 20a, 20b and/or the delivery tube 14. In some constructions, the cannula device 18a, 18b may further include a handle connector 48a, 48b serving as a proximal end of the corresponding cannula 22a, 22b. The handle connector 48a, 48b may simply be an extension of the cannula 22a, 22b. Alternatively, the handle connector 48a, 48b may incorporate features forming part of a locking mechanism component of the system 10. For example, the handle connector 48a, 48b may include a luer-lock type of connector, but other known connecting mechanism may be successfully interchanged (e.g., a conventional threaded hole, a threaded locking nut arrangement, etc.). Features of one suitable locking mechanism are described in U.S. Pat. No. 7,922,690, which is incorporated herein by reference in its entirety.

The cavity-forming devices 20a, 20b may be substantially identical and may assume various forms appropriate for forming a void or cavity within bone. In this regard, each of the cavity-forming devices 20a, 20b includes an elongated body 60a, 60b distally connected to or forming a working end 62a, 62b. The elongated body 60a, 60b is sized to be slidably inserted within the lumen 44a, 44b of the corresponding cannula 22a, 22b, and may include one or more tubes, shafts, etc., necessary for operation of the corresponding working end 62a, 62b. Thereafter, a proximal region 64a, 64b of the elongated body 60a, 60b may be connected to or form a cannula connector 66a, 66b. The cannula connector 66a, 66b may assume various forms conducive for selective, rigid attachment to the corresponding handle connector 48a, 48b as described above (e.g., the cannula connector 66a, 66b and the corresponding handle connector 48a, 48b collectively form a locking mechanism), and thus may include or contain a luer-lock threaded fitting. Alternatively, the cannula connector 66a, 66b may be omitted, and depth markings (not shown) included along an exterior of the proximal region 64a, 64b that facilitate desired locating of the working end 62a, 62b relative to the corresponding cannula 22a, 22b as described below.

The working end 62a, 62b may include one or more components appropriate for forming a cavity or void within bone. For example, in some constructions, the working end 62a, 62b may include one or more expandable or inflatable members (e.g., a single balloon, multiple balloons, a single balloon with two or more discernable inflation zones, etc.) constructed to transition between a contracted (e.g., deflated) state in which the working end/balloon 62a, 62b may be passed through the corresponding lumen 44a, 44b, and an expanded (e.g., inflated) state in which the working end/balloon 62a, 62b expands and compacts contacted cancellous bone. In this regard, a size and shape of the working end/balloon 62a, 62b may be predetermined and/or restrained with one or more additional components (not shown), such as internal and/or external restraints. In preferred embodiments the working end/balloon 62a, 62b will be structurally robust, able to withstand (e.g., not burst) at expected inflation pressures and when in contact with bone. Further, the first working end 62a and the second working end 62b may be identical or different.

The working ends/balloons 62a, 62b may be exteriorly coated with a material configured to resist bonding with the curable material being delivered to the vertebra 30. The anti-sticking coating may assume various forms as a function of the selected curable material, and in some embodiments is a silicone coating. Other materials exhibiting aversion to bonding with bone cement are also envisioned, for example, polypropylene. In related embodiments, a thin-walled expandable sleeve constructed of the selected anti-sticking material (e.g., a polypropylene sleeve) may be disposed over the working end/balloon 62a, 62b. Though not shown, one or both of the cavity-forming devices 20a, 20b may include a valve or similar component that operates to selectively seal the working end/balloon 62a, 62b.

The cavity-forming devices 20a, 20b each further include one or more additional components connected or operable through the proximal region 64a, 64b for actuating the corresponding working end 62a, 62b. By way of one non-limiting example, each of the cavity-forming devices 20a, 20b may include a source 68a, 68b of pressurized fluid (e.g., contrast medium) for inflating the balloon(s) carried or formed by the corresponding working end 62a, 62b. A hand-held, syringe-type pump may be used as the pressurized source. In other embodiments, a single one of the sources of pressurized fluid 68a or 68b may be provided and employed to inflate both of the working ends/balloons 62a, 62b individually. Appropriate balloon-inflation systems are well known and will readily be apparent to those of skill in the art.

Where provided, the delivery tube 14 is sized for insertion within the lumens 44a, 44b, and defines a distal tip 80 and a proximal section 82. As described below, the delivery tube 14 may be employed to deliver curable material to the target site. Thus, the delivery tube 14 has an outer diameter that is smaller than a diameter of the lumens 44a, 44b; however, the outer diameter of the delivery tube 14 preferably will not be so small as to allow curable material to readily travel around the outside of the delivery tube 14 and back into the corresponding cannula 22a, 22b.

A cannula connector 84 may be coupled to, or formed by, the proximal section 82 of the delivery tube 14. The cannula connector 84 is akin to the cannula connector 66a, 66b described above (e.g., combines with the selected handle connector 48a, 48b to form a locking mechanism), and thus may assume any of the forms previously described. Alternatively, the delivery tube 14, where provided, may form depth markings (not shown) along the proximal section 82 that facilitates desired locating of the distal tip 80 relative to the cannula 22a, 22b during use.

The delivery tube 14 is configured for fluid coupling to the curable material source 16. In some embodiments, a portion of the delivery tube 14 projects proximally beyond the cannula connector 84, and is fluidly coupled to the curable material source 16, for example via an injection connector 86. Alternatively, auxiliary tubing 88 may be provided with the curable material source 16, and fluidly connected to the delivery tube 14 via the cannula connector 84. In yet other embodiments, the delivery tube 14 is omitted, and the curable material source 16 connected directly to the handle connector/proximal end 48a, 48b (e.g., the auxiliary tube 88 is connected to the connector 48a, 48b; or the tubing 88 eliminated and the curable material source 16 (e.g., a syringe) directly coupled to the connector 48a, 48b).

The curable material source 16 may assume various forms appropriate for delivering the desired curable material, and may typically comprise a chamber filled with a volume of curable material and employing any suitable injection system or pumping mechanism to transmit curable material out of the chamber and through the delivery tube 14. Typically, a hand injection system is used where a user applies force by hand to an injector. The force is then translated into pressure on the curable material to flow out of the chamber. A motorized system may also be used to apply force.

Although the system 10 has been described as including the single source of curable material 16, in other constructions, a separate source of curable material 16 may be provided for each of the delivery assemblies 12a, 12b. Similarly, two (or more) of the delivery tubes 14 may be included. Along these same lines, the system 10 may be configured such that the curable material source 16 is directly connected to one or both of the cavity-forming devices 20a, 20b (e.g., the elongated body 60a of the first cavity-forming device 20a may form or terminate at a nozzle proximate (e.g., distal) the working end 62a and through with the curable material may be directly dispensed).

The system 10 and other systems and methods disclosed herein will be useful in performing a wide variety of height restoration and bone stabilization procedures as part of an overall curable material delivery procedure. As such, FIGS. 2A-3B illustrate use of the system 10 in restoring the height of, and delivering curable material into, a target site of a vertebra 100. In general terms, the vertebra 100 includes pedicles 102a, 102b and a vertebral body 104 defining a vertebral wall 106 surrounding bodily material 108 (e.g., cancellous bone, blood, marrow, and soft tissue). The pedicles 102a, 102b extend from the vertebral body 104 and surround a vertebral foramen 110. As a point of reference, systems of the present disclosure may be suitable or readily adapted by those of skill in the art for accessing a variety of bone sites. Thus, although the vertebra 100 target site is illustrated, it is to be understood that other bone sites may be accessed and treated by the system 10 (e.g., femur, long bones, ribs, sacrum, etc.).

The first and second cannulas 22a, 22b may be employed to form first and second access paths to first and second target site locations 120a, 120b. For example, the cannulas 22a, 22b are inserted in a bipedicular fashion through respective ones of the pedicles 102a, 102b and into the bodily material 108. The cannulas 22a, 22b provide access to the corresponding target site 120a, 120b at the open distal ends 42a, 42b thereof. One or more stylets (not shown) may be employed to assist in forming/accessing the target sites 120a, 120b. For example, a series of differently-sized or configured (e.g., sharpened and blunt) stylets may be successively delivered through the respective cannula 22a, 22b to form a channel to the target site 120a, 120b. Alternatively, or in addition, an outer guide cannula (not shown) may be deployed to form an access path for subsequent insertion of the cannulas 22a, 22b.

After the cannulas 22a, 22b are positioned within the bodily material 108 at the desired target sites 120a, 120b, the cavity-forming devices 20a, 20b are assembled to the corresponding cannula 22a, 22b. For example, and as shown in greater detail in FIG. 2B, the elongated body 60a, 60b is slidably inserted within the corresponding cannula 22a, 22b, with the respective working end 62a, 62b being distally advanced therethrough. More particularly, with configurations in which the working end 62a, 62b is a balloon or other expandable member format, the working end/balloon 62a, 62b is transitioned to a contracted state (e.g., deflated) so as to be slidably received through the lumen 44a, 44b. The elongated body 60a, 60b is positioned relative to the corresponding cannula 22a, 22b such that the respective working end/balloon 62a, 62b extends distal the corresponding cannula distal end 42a, 42b. For example, where the elongated body 60a, 60b may include depth markings as described above, the appropriate depth marking will be aligned with the corresponding handle connector 48a, 48b (FIG. 1), thereby ensuring that the working end/balloon 62a, 62b is fully deployed or extended beyond the corresponding cannula distal end 42a, 42b. In other constructions, upon connection of the cannula connector 66a, 66b and the corresponding handle connector 48a, 48b, the working end/balloon 62a, 62b is distal the corresponding distal end 42a, 42b and is positioned at the corresponding target site 120a, 120b. Placement of the cavity-forming devices 20a, 20b may be performed simultaneously or consecutively.

Figure 2C:
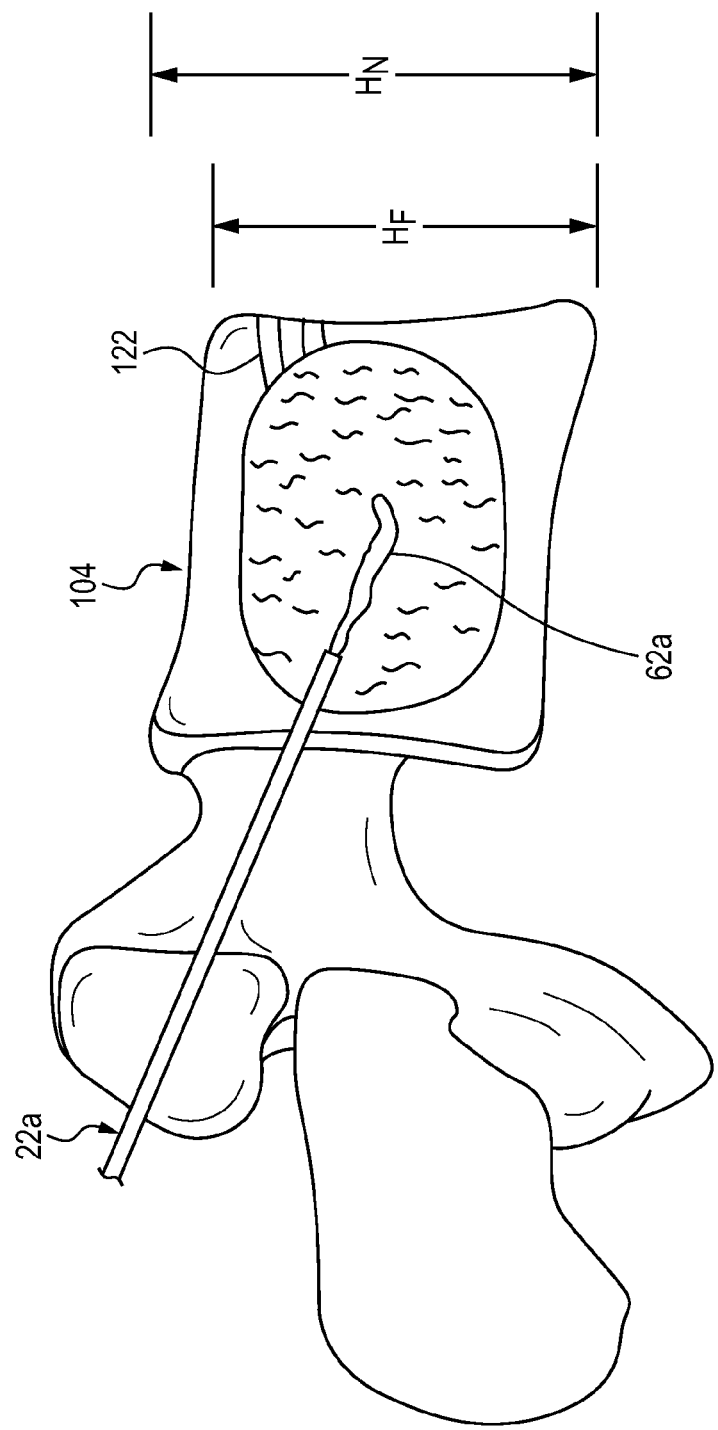
FIG. 2C is a lateral view of the vertebral body of FIGS. 2A and 2B.

As a point of reference, FIG. 2C provides a lateral view of the vertebral body 104 in which the first working end/balloon 62a has been deployed (and in the contracted state). As shown, the vertebral body 104 is fractured (referenced generally at 122) and thus exhibits a fractured height $H_F$ that is less than a natural or native height $H_N$ (designated generally).

Figure 3A:
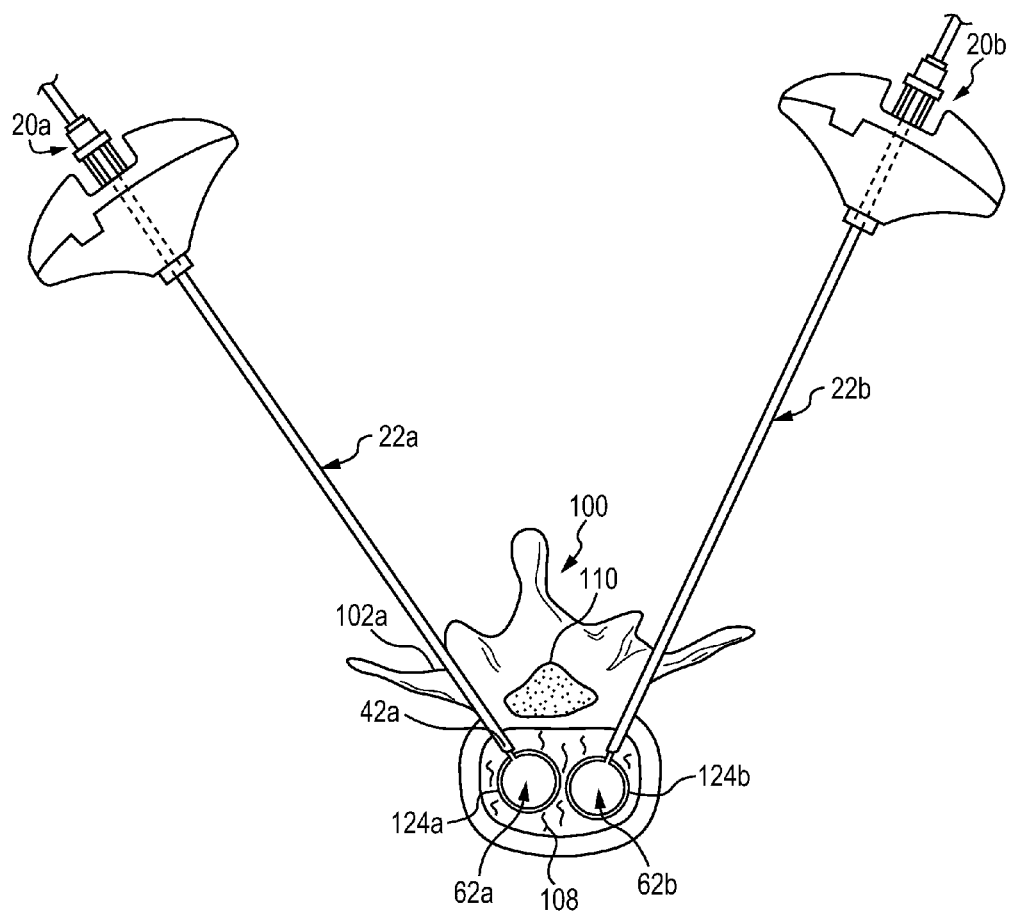
FIGS. 3A-3B illustrate the system of FIG. 1 in further performing the height restoration and curable material delivery procedures with a bipedicular dual-balloon method.
Figure 3B:
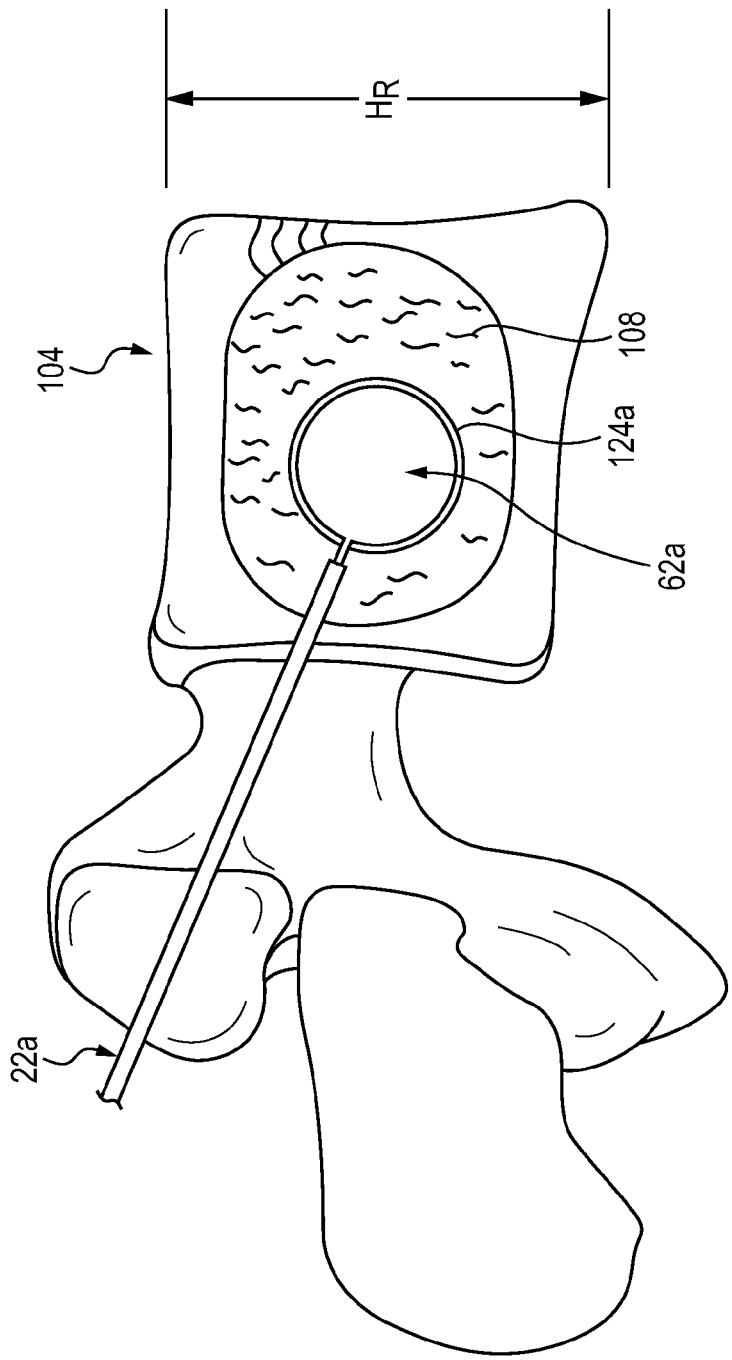

With reference to FIG. 3A, the cavity-forming devices 20a, 20b are operated to cause the corresponding working ends/balloons 62a, 62b to form first and second cavities or voids 124a, 124b, respectively, in the bodily material 108. For example, the working ends/balloons 62a, 62b may be expanded (e.g., inflated) substantially simultaneously. Alternatively, with embodiments in which a single inflation source 68a or 68b (FIG. 1) is provided, the first working end/balloon 62a is inflated and then sealed in the expanded or inflated state. The inflation source 68a or 68b is then fluidly connected to the second working end/balloon 62b and operated to cause expansion thereof. Following expansion of the working ends/balloon 62a, 62b, the expanded working ends 62a, 62b are both supporting the vertebral body 108. In this regard, and as best illustrated in FIG. 3B, expansion of the working ends/balloons 62a, 62b not only forms the cavities 124a, 124b, but also restores or enhances a height of the fractured vertebral body 104. More particularly, a restored height $H_R$ is established that beneficially approximates the natural height $H_N$. The restored height $H_R$ may be the same as, slightly less than, or slightly greater than, the natural height $H_N$ (FIG. 2C); in any event, the restored height $H_R$ will be greater than the fractured height $H_F$ (FIG. 2C).

Returning to FIG. 3A, the second cavity-forming device 20b is then operated to transition the second working end/balloon 62b from the expanded state to the contracted state (e.g., the second balloon 62b is deflated). In the contracted state of the second working end/balloon 62b, the second cavity-forming device 20b may be removed from the second cannula 22b.

Figure 4A:
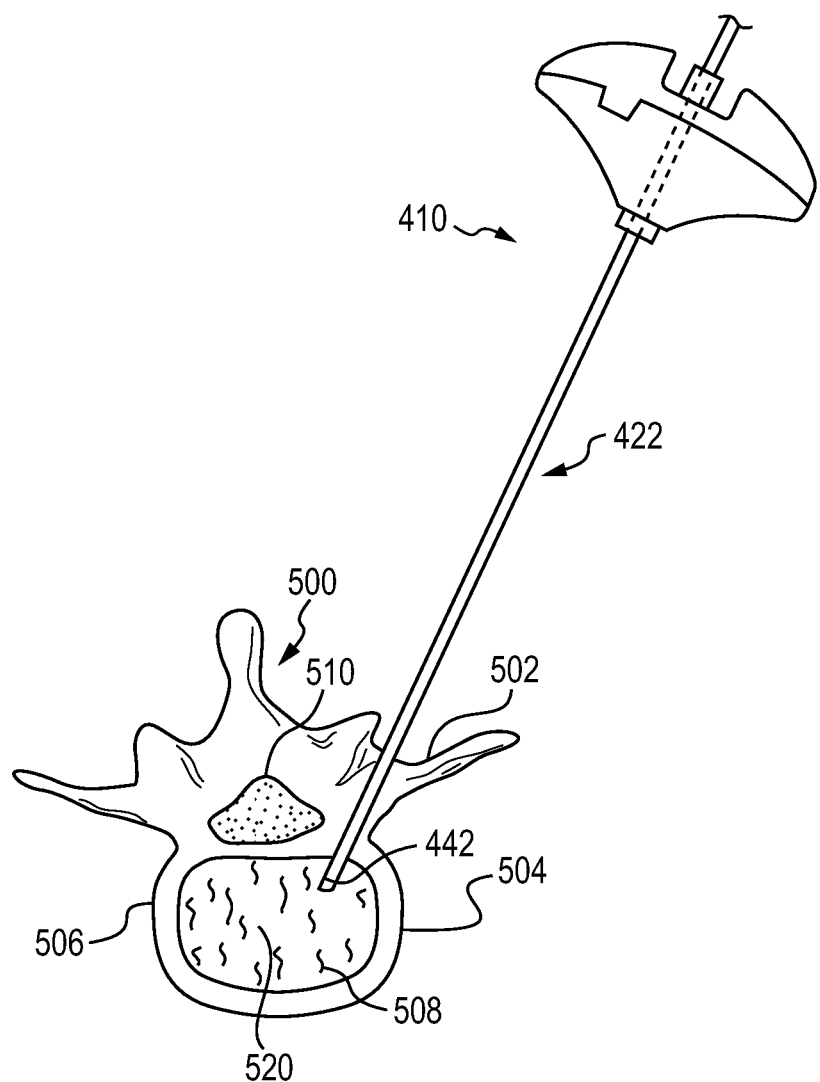
FIGS. 4A-4H illustrate a system and method for transpedicular or parapedicular access providing stylet-guided, generally centralized location of a cavity/void and curable material placement therein.

Other embodiments of a system and method for bone augmentation are described with reference to FIGS. 4A-4H. A system 410 is illustrated in FIG. 4A that may be similar or identical in most respects to the system 10 described above, and corresponding reference numbers should be understood as analogous. Those of skill in the art will appreciate that system components described above with reference to FIGS. 1-3B and in the various incorporated references may be used with the embodiments described below within the scope of the present disclosure. The system includes an access cannula 422 (preferably generally straightline in configuration), which is shown as engaged into a cancellous bone-including region 508 (that may also include marrow and other body material as noted above with reference to FIGS. 2A-3B) of a vertebra 500 via a vertebral pedicle 502 thereof. The distal end 442 of the access cannula 422 has been directed near a target region/site 520 that is generally central within the bone region 508. A portion of the bone region 508 may be at least partially defined by a cortical rim 506 forming a boundary of the anterior vertebral body 504.

The target site 520 may be identified by a physician preparing for a vertebroplasty procedure. Identification of the target site may include generally determining a central location in the cancellous bone portion of the vertebra 500 that will substantially or at least generally support height-restoration and/or structural augmentation that preferably is at least generally symmetrical with respect to the vertebra and particularly with respect to damaged portion(s) thereof. Generally, the target site may be approximately centered within the bone structure. However, the target site is defined more generally as a pre-determined location within a bone structure that may be determined by treating personnel to provide for symmetrical application of force to treat a bone.

Figure 4B:
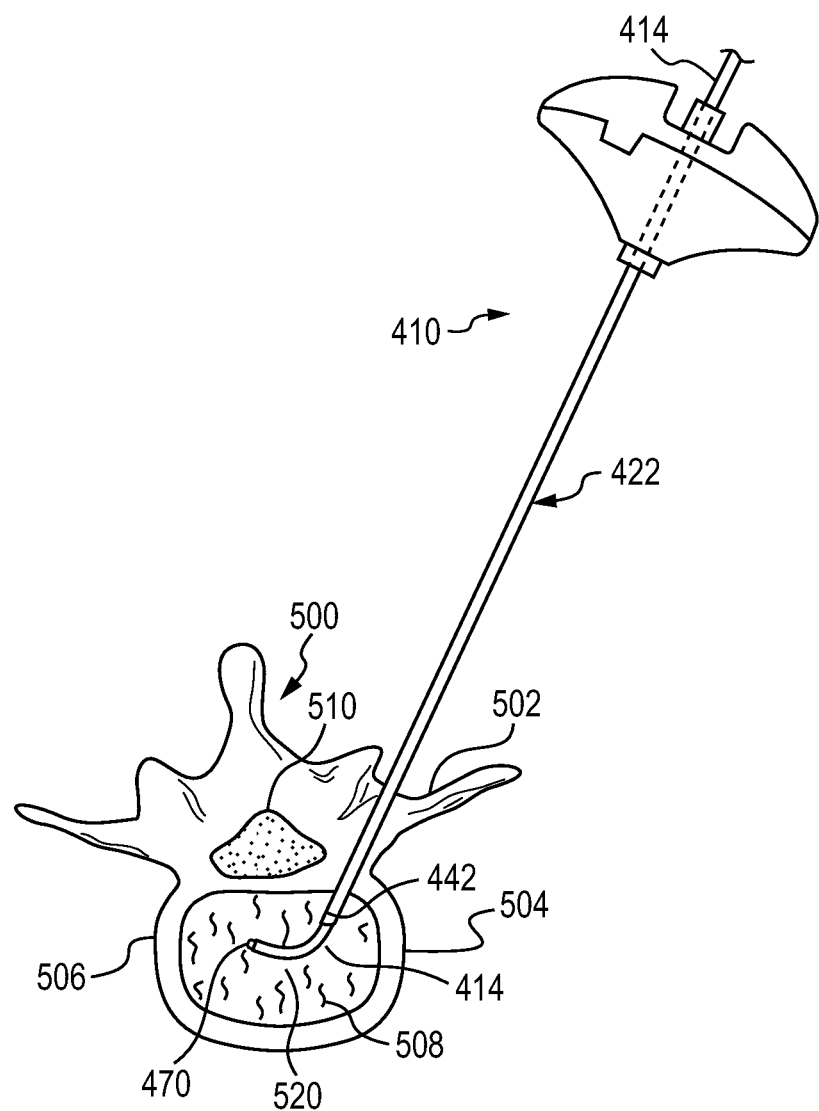

As shown in FIG. 4B, a stylet 470 may be directed through the access cannula 422. The stylet 470 snugly but slidably extends through an overlying delivery tube 414 that preferably is made a flexible polymer having some columnar strength (e.g., polypropylene, PEEK) that will maintain a patent longitudinal lumen upon withdrawal therefrom of the stylet 470. In some embodiments, the delivery tube may include a metal needle with a distal curved length and a distal terminus end opening through which the expandable member is deployed where the metal needle curve and the stylet curve are about the same when unconstrained and are constrained to a generally straightline orientation when constrained during passage through the access cannula. In some embodiments, the delivery tube may include a metal needle with a distal curved length and a distal-most straight length open at its distal terminus and configured to allow an expandable member to be deployed therefrom without significantly curving the expandable member during its deployment. The delivery tube 414 may include at least one radio-opaque marker (e.g., near its distal end) and/or one or more visual indicia near its proximal end providing for user-observation regarding its distal end position relative to the access cannula of the system. The at least one radio-opaque marker includes that the delivery tube may itself be partially or wholly radiopaque. For example, in certain preferred embodiments, a PEEK (or other polymer) delivery tube 414 may be extruded with Barium in it (e.g., in the form of barium sulfate or another radiopaque material), such that some or all of the entire tube is radiopaque, obviating the need for other radio-opaque indicia.

The stylet 470 preferably is constructed including a memory metal material having a pre-set curve near its distal end. In this manner, the stylet 470 can be deflected to a generally straight orientation while it is being directed through the access cannula 422. The stylet and the delivery tube have sufficient length to extend through and be operable beyond the distal end 442 of the access cannula. Thus, as shown in FIG. 4B, in the time and space that the stylet 470 is advanced out of the distal end 442 of the access cannula 422, its pre-set curve is re-asserted such that the stylet 470 and overlying delivery tube 414 curve into the target region 520. The pre-set curve of the stylet 470 may be offset from its distal end sufficiently to provide a generally straightline portion of the stylet distal of its pre-set curve. A proximal-end structure of the stylet 470 may include indicia 471 showing the direction of curvature of the pre-set curve (FIG. 4C).

In certain embodiments, a system may include a plurality of stylets, each having a different pre-set curve. In this manner, a physician may determine a desirable stylet curvature to reach the target region and select an appropriate stylet. Each stylet may be individually packaged and clearly marked with size and/or curvature, as well as providing other visual indicia of properties of interest to a physician. In use, the physician may determine a desired curvature path between the distal end 442 of the access cannula and the approximate center of the target site (e.g., in the middle of the predetermined location, which may or may not be generally centered within a bone portion), select a guide stylet including a distal preset curve corresponding to said curvature path from a plurality of guide stylets having different preset curvatures, and insert the selected stylet through the delivery tube before directing the assembled stylet and overlying tube to the target site.

Figure 4C:
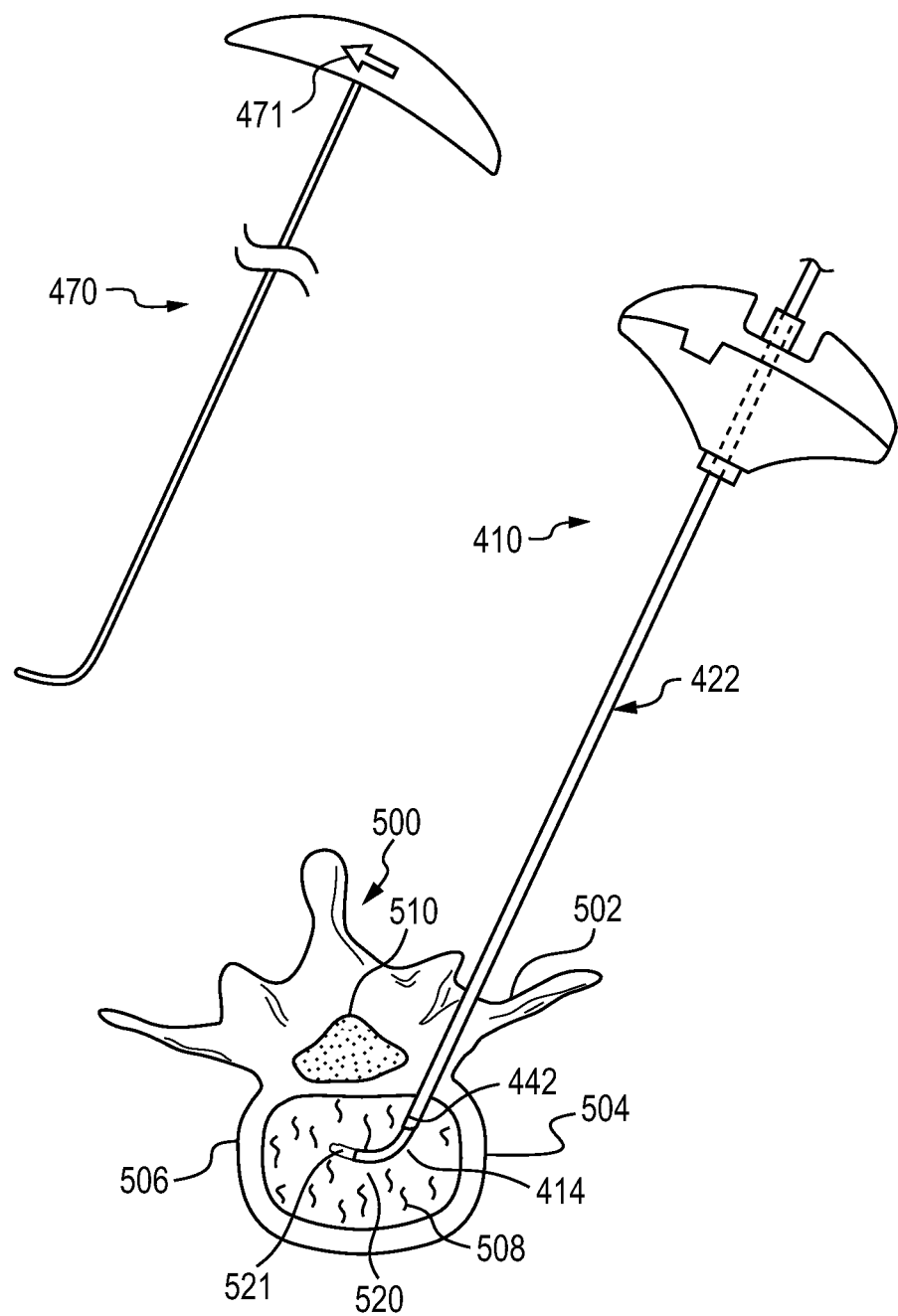
Figure 4D:
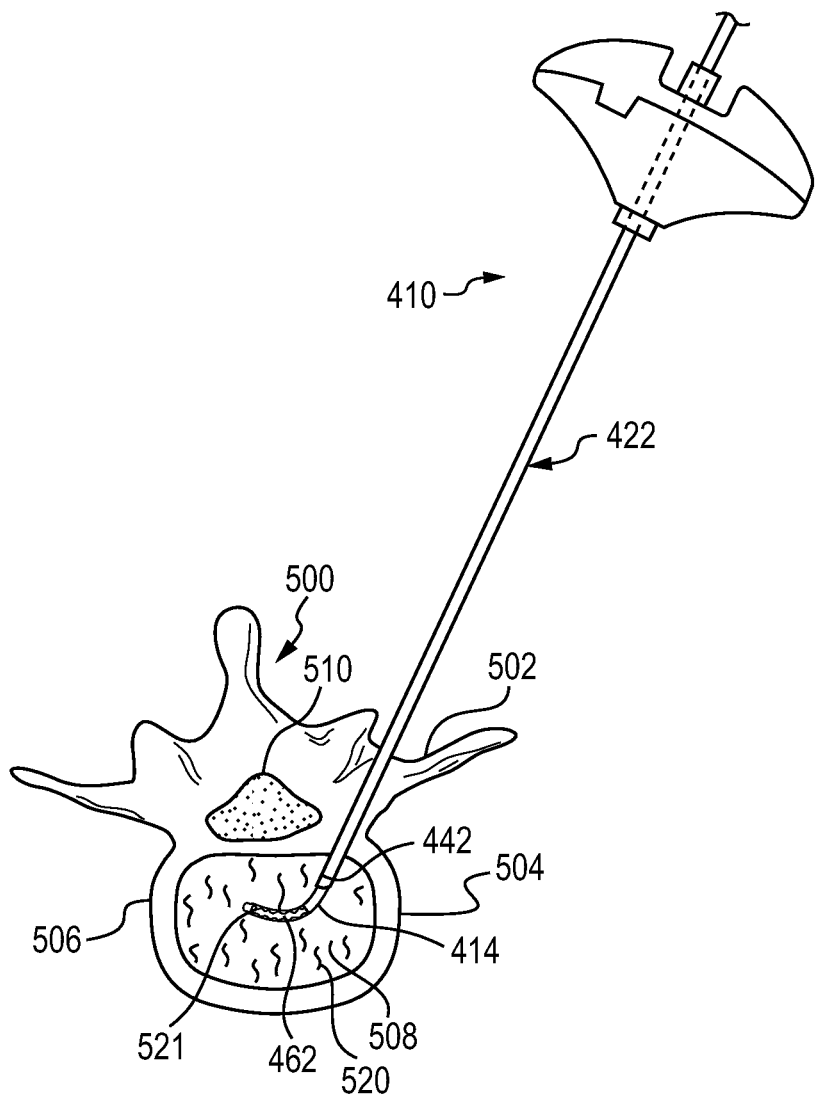
Figure 4E:
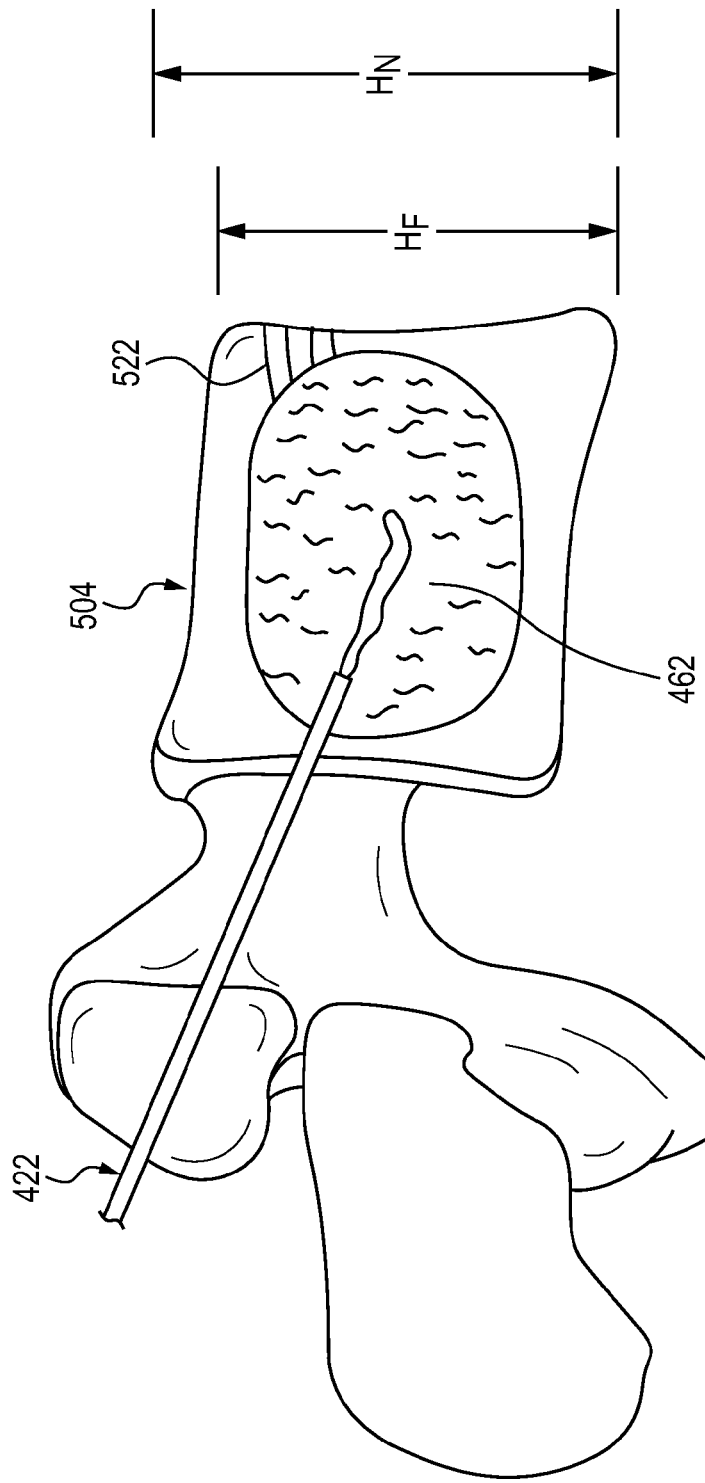

As shown in FIG. 4C, the stylet 470 may be withdrawn from the delivery tube 414 (which is shown as slightly retracted from its furthest extension point) after having created a generally tubular path or void 521 in the material 508 in the target region 520. Thereafter, as shown in FIG. 4D, a cavity-forming device, which may include a working end embodied as—for example—a distal balloon 462, may be directed into the path 521 formed by the stylet 470. A wire or other support structure (not shown) may be provided in the cavity-forming device end 462 to enhance its trackability and pushability through/into the path 521. As a point of reference, FIG. 4E provides a lateral view of the vertebral body 504 wherein the working end/balloon 462 has been deployed (and is still in a contracted state). As shown, the vertebral body 504 being treated is anteriorly fractured (referenced generally at 522) and thus exhibits a fractured height $H_F$ that is less than a natural or native height $H_N$ (designated generally).

In one preferred embodiment of a method, the delivery tube 414 may be extended all the way to the end of a cavity/void 521 formed with the stylet 470. Thereafter, the cavity-forming device may be extended through the delivery tube 414 until its working end/balloon 462 contacts the bone at the distal end thereof. This may protect, e.g., a balloon or other distal expandable member of the cavity forming device from external damage during introductory movement and provide for its placement in a desired location and orientation. Thereafter, the delivery tube 414 may be withdrawn sufficiently to allow cavity-forming expansion of the working end/balloon 462 as described below. Those of skill in the art will appreciate that one or more of the cavity-forming device, working end/balloon 462 thereof, and the delivery tube may include visual indicia (e.g., markings on the user-held end, radio-opaque indicia at or near the distal end) that enable a user to determine the relative positions of those components to perform a method as described. In this or other embodiments, the inner diameter of the delivery tube 414 and/or the external surface(s) of the cavity forming device(s) may be lubriciously coated (e.g., with silicone, PTFE, and/or another lubricious material).

Figure 4F:
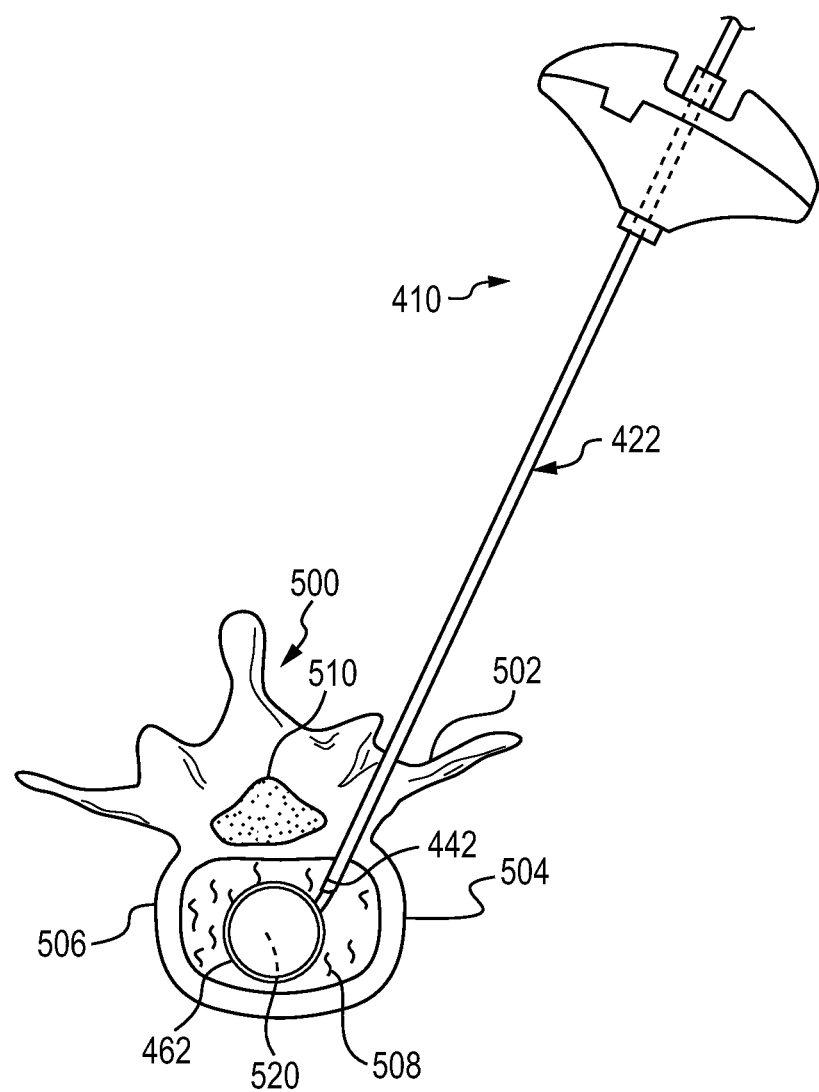
Figure 4G:
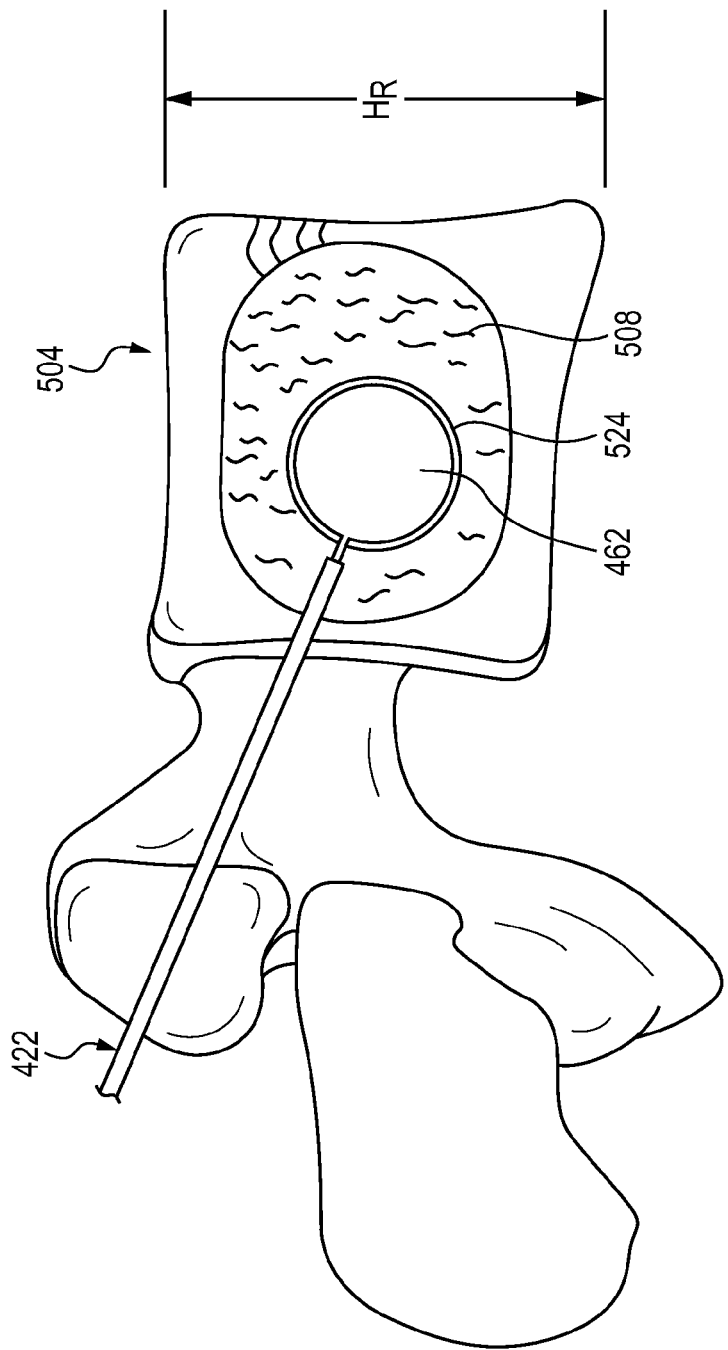

With reference to FIG. 4F, the cavity-forming device may be operated to cause its corresponding working end/balloon 462 to form a (preferably approximately, generally, or substantially centered) cavity/void in the body material 508. For example, the working end/balloon 462 may be expanded (e.g., inflated). As best illustrated in FIG. 4G, expansion of the working end/balloon 462 not only forms the cavity, but may also restore or enhance a height of the fractured vertebral body 504. More particularly, a restored height $H_R$ is established that may beneficially approximate the natural height $H_N$. Such a restored height $H_R$ may be the same as, slightly less than, or slightly greater than, the natural height $H_N$ (FIG. 4E); in any event, any restored height $H_R$ will be greater than the fractured height $H_F$ (FIG. 4E). If desired for fluoroscopic visualization, radio-opaque contrast material may be provided into the cavity, internal to or external of the expandable member. Transpedicular access for kyphoplasty at a target site approximately centered in the cancellous bone may not be easily achievable without the curved stylet approach of the present disclosure. The limits of patient anatomy, the desirability of minimizing procedure time (for the sake of, e.g., cost and patient health), and the desirability of minimizing patient recovery time all provide for advantages of the present methods and systems.

Figure 4H:
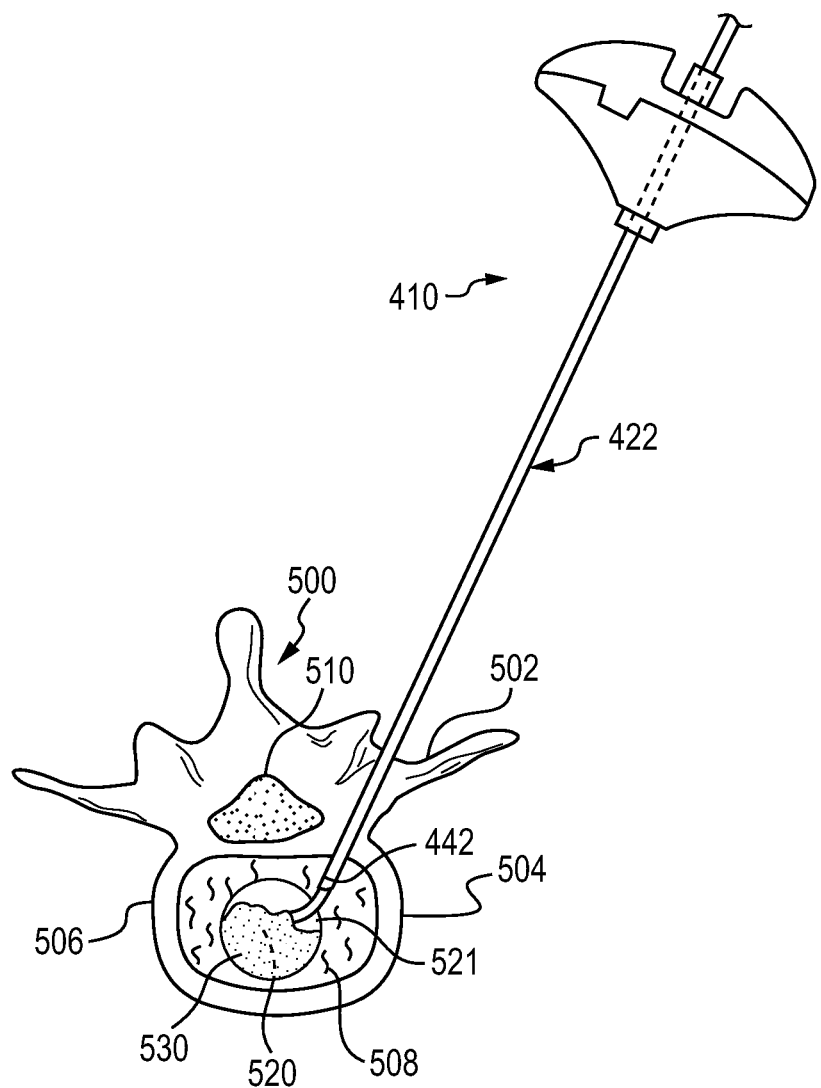

Thereafter, the expandable member's working end/balloon 462 may be withdrawn. Then, as shown in FIG. 4H, curable material 530 may be delivered into the cavity via the delivery tube 414. In this or other embodiments, the curable material may delivered in a more targeted manner via a curved delivery cannula directed though the access cannula into the cavity. In such an embodiment, the delivery tube 414 may be removed as an intermediate step before introducing the curved delivery cannula, or the curved delivery cannula can be directed through the delivery tube 414.

Methods and devices for use in introducing curable material via a curved access cannula in a manner useful within the presently disclosed systems and methods are disclosed in U.S. Pat. Nos. 7,713,273; 7,799,035; 8,128,633; and 8,226,657, as well as U.S. Pat. App. Publ. No. 2010/0087828, each of which is incorporated herein by reference in its entirety. It should be understood and appreciated that the "delivery cannula" described therein may include a pre-set curve with structure and function described herein in reference to a "stylet." As such the term "stylet" as used herein is defined to include a delivery cannula that has an internal delivery lumen dimensioned and oriented for delivering curable material. This definition may therefore, in some embodiments, provide a stylet that is embodied as a delivery cannula, while—in other embodiments—provide a stylet separate from a delivery cannula. Specifically, in the methods described above, and those described below, a delivery cannula or stylet, which may be embodied as an AVAflex® Curved Vertebral Augmentation Needle (CareFusion Corp., San Diego, Calif.), can be used. In this manner the curable material will be directed through the lumen of the cannula/stylet (e.g., stylet 470) into the space created by an expandable device.

Stated differently, a delivery cannula may be provided with temperature-dependent multi-curve structure and function. This cannula may further include an overlying delivery tube 414 and be operated in the manner described above for a stylet, except that the curable material may be introduced through the delivery cannula (e.g., after it is withdrawn; the expandable member is introduced, activated, and withdrawn; then the delivery cannula—potentially pre-loaded with curable material—is reintroduced).

In some embodiments, a delivery cannula may include a closed distal end terminus and a side-facing opening near the terminus, where the opening is oriented along an outside surface of the curved portion of the delivery cannula near its closed distal end terminus. It may also include proximal-end indicia that show the direction of distal cannula curvature. The curvature of the delivery cannula may be configured to correspond to the pre-set curve of a separate stylet 470, or the stylet 470 may—instead of being constructed as a solid-cross-section stylet—be constructed as a/the precurved delivery cannula as described above. In some embodiments, the delivery cannula/stylet may be pre-loaded with curable material before the delivery cannula is directed through the guide cannula, in order to decrease procedure time and reduce the likelihood of a bolus during introduction of the curable material.

A method for single-access-point provision of one or a plurality of generally distinct or continuous cavity(ies) is described with reference to FIGS. 4A-4H and FIGS. 5A-9. The method may be used different bones of a patient body, and the method here is illustrated with access through a single pedicle of a patient vertebra. A single unipedicular access path may allow the physician to stabilize both the upper and lower vertebral endplates. This method could stabilize a cleft fracture and then create a void in other location of the vertebral body.

Figure 5A:
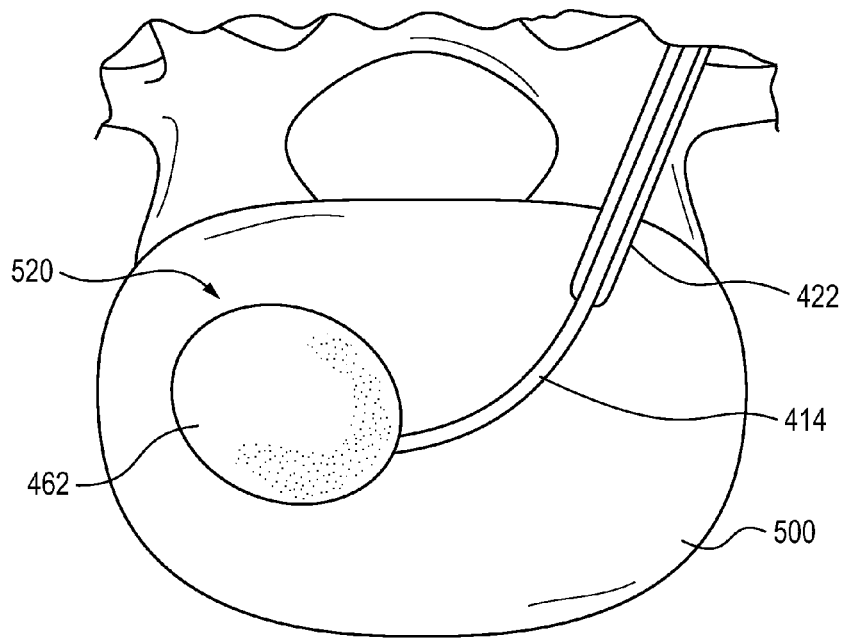
FIGS. 5A-5D depict a method of bone augmentation including forming and filling a plurality of cavities through a single access point.

In one embodiment of a method, an expandable member, which may be embodied as a balloon 462, may be directed to a target region 520 in the manner described above with reference to FIGS. 4A-4E, where the balloon 462 is within a delivery tube 414. The target site 520 may be well across a left-right lateral midline, and the balloon 462 inflated as shown in FIG. 5A. Next, the balloon 462 may be deflated to leave a first cavity 540.

Figure 5B:
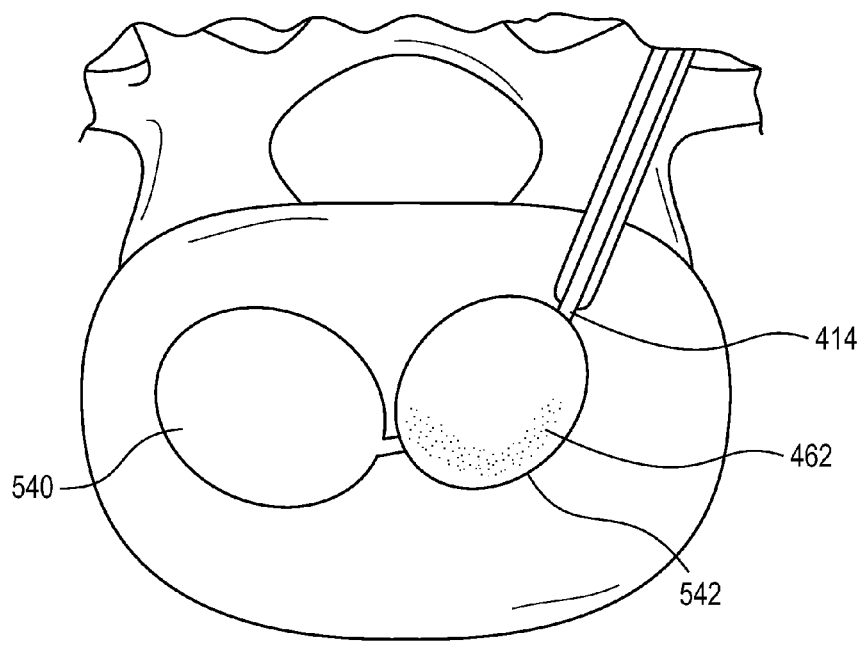
Figure 5C:
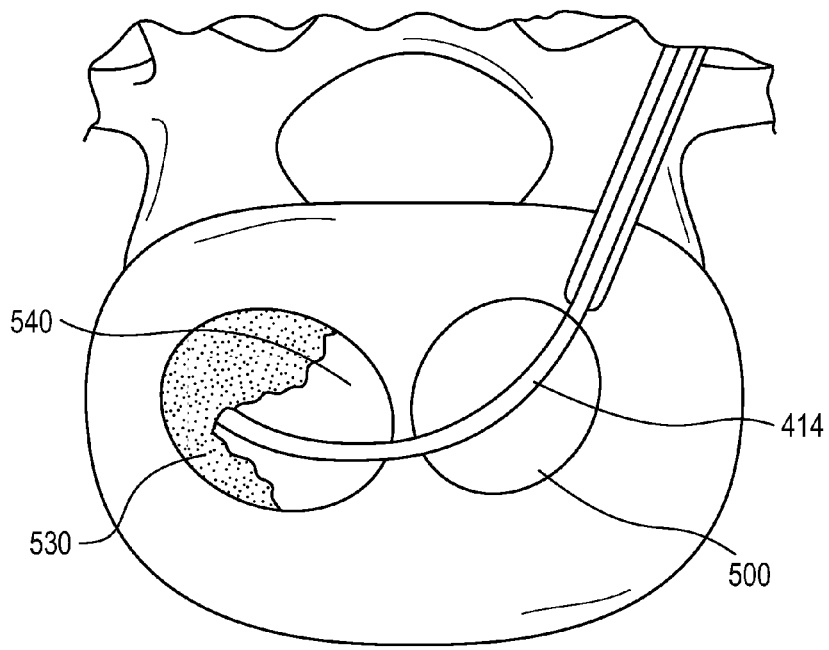

Thereafter, the delivery tube 414 can be retracted with the balloon 462 to position the balloon 462 in a desired location. In the event that the balloon was withdrawn into the lumen of the delivery tube 414, the delivery tube may be further retracted to expose and allow the balloon 462 to be reinflated as shown in FIG. 5B, forming a second cavity 542. In the method step illustrated in FIG. 5C, the delivery tube 414 is advanced into the first cavity 540, where curable material 530 may be delivered via the delivery tube 414.

In a preferred variant of the method, the delivery tube 414 may be completely withdrawn along with the balloon 462, and the curable material may be delivered via a delivery cannula. The delivery cannula may be embodied, for example, as the stylet discussed above (e.g., as a shape-memory stylet, such as—for example—used in the AVAflex® system) advanced into and through the cavities in the absence of the delivery tube 414, then retracted during progressive delivery of curable material. In another variant method, a delivery cannula/stylet may be disposed through the delivery tube 414 after the balloon 462 has been completely withdrawn following formation of the desired cavities.

Figure 5D:
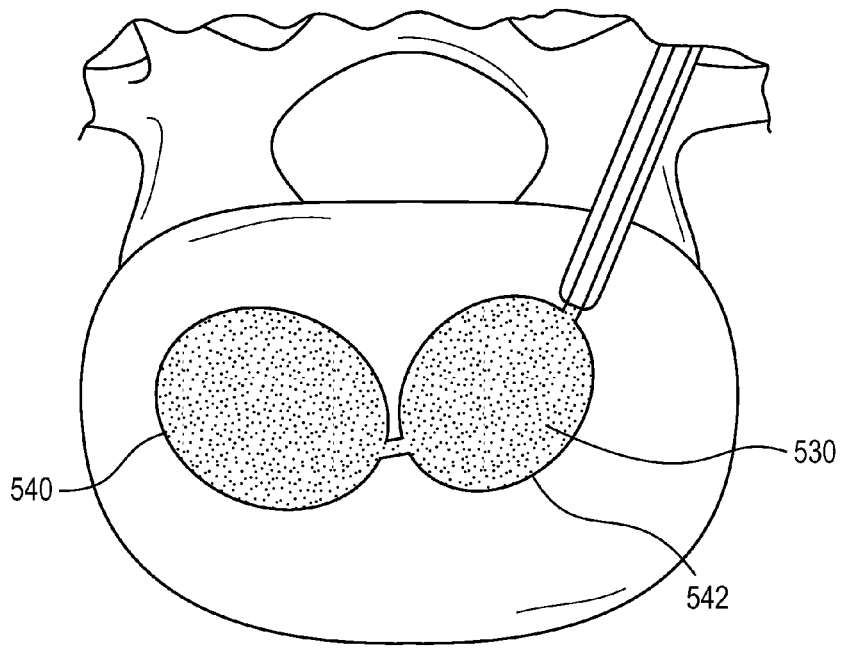

Then, the delivery tube 414 (or other delivery device, such as a delivery cannula/stylet/needle) may further be withdrawn while still delivering curable material 530 sufficient to fill the first cavity 540 and the second cavity 542, generally separate from the first cavity, as shown in FIG. 5D. In some embodiments, less than the entire cavity may be filled. That is, as noted above, in certain embodiments where injection of curable material is effected through a stylet, the stylet may be disposed through the delivery tube 414, or the delivery tube may be completely withdrawn along with the balloon, after which a delivery cannula/stylet (shown parenthetically in the alternative as reference 470, although a preferred delivery stylet will actually deliver curable material from a side aperture) is advanced into the position of the delivery tube 414 shown in FIG. 5C and curable material is delivered therethrough as illustrated, with the delivery cannula/stylet (not shown) being retracted during material delivery. Stated differently, in FIGS. 5C and 5D, the curable material delivery structure labeled with reference number 414 may instead be embodied as a delivery cannula/stylet (such as, for example, an AVAflex® needle/cannula/stylet of the type described above).

Figure 6:
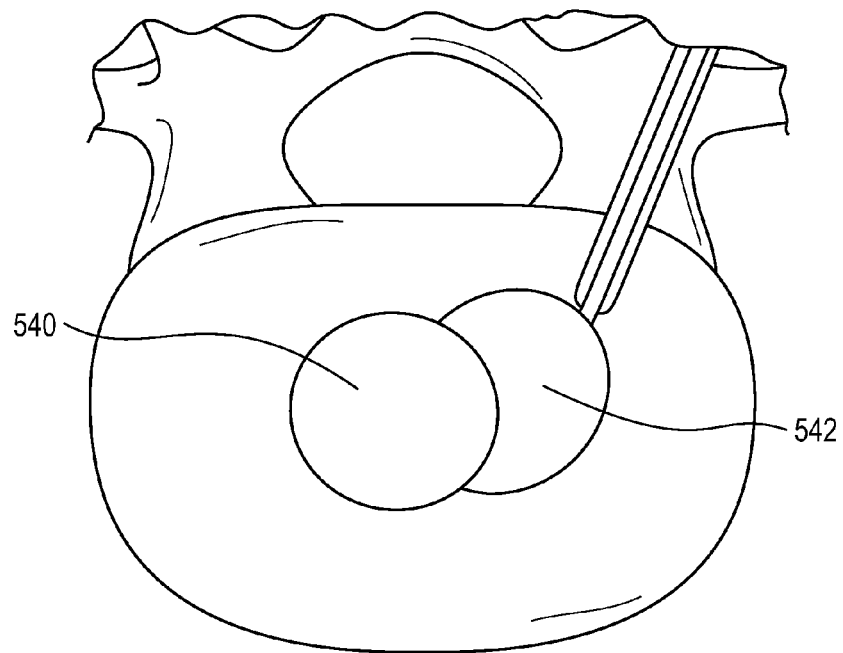
FIG. 6 shows a two-cavity implementation of the presently described methods where the cavities are substantially continuous so as to form a larger single cavity.
Figure 7:
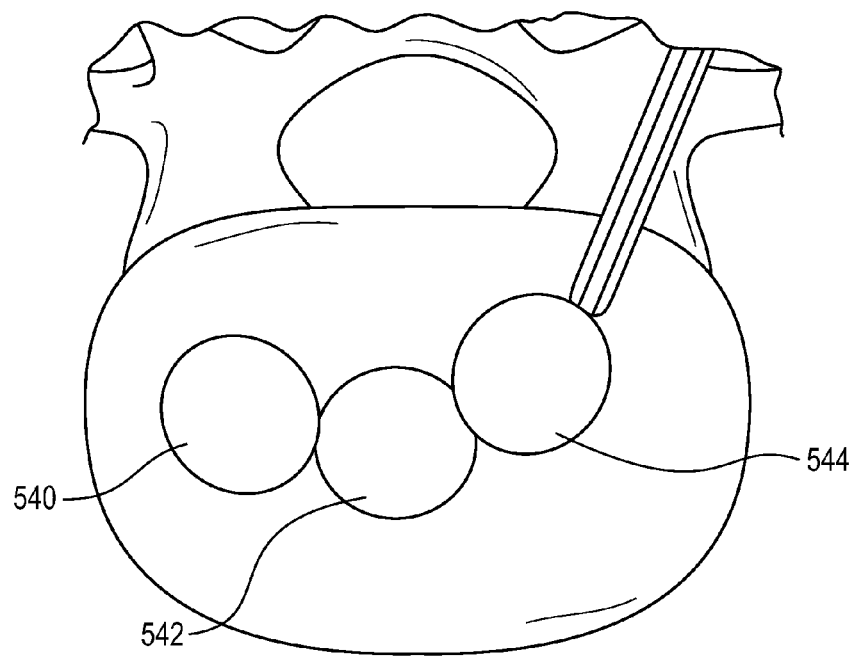
FIGS. 7 and 8 show, respectively top and side views of a three-cavity implementation of the described methods.

Those of skill in the art will appreciate that, in other embodiments of the method, two, three or more cavities may be formed in this manner. The cavities may be generally separate and distinct, as shown in FIG. 5D and, somewhat less separate, in FIG. 7, or they may overlap: that is, the serial inflation/deflation of the balloon 462 may be done to form an overlapping series of generally continuous cavities, as shown in FIG. 6, such that the result is generally a single larger overall cavity. Each of FIGS. 5A-7 shows a top-down view of a vertebra. However, it should be appreciated that the offset of a plurality of cavities in a bone mass may also be manifested in an anterior-posterior aspect (whether vertebral, as illustrated, or in a different bone type such as a long bone (e.g., femur), other irregular bone (e.g., sacrum), flat bone (e.g., a pelvic bone), or other bone type).

Figure 8:
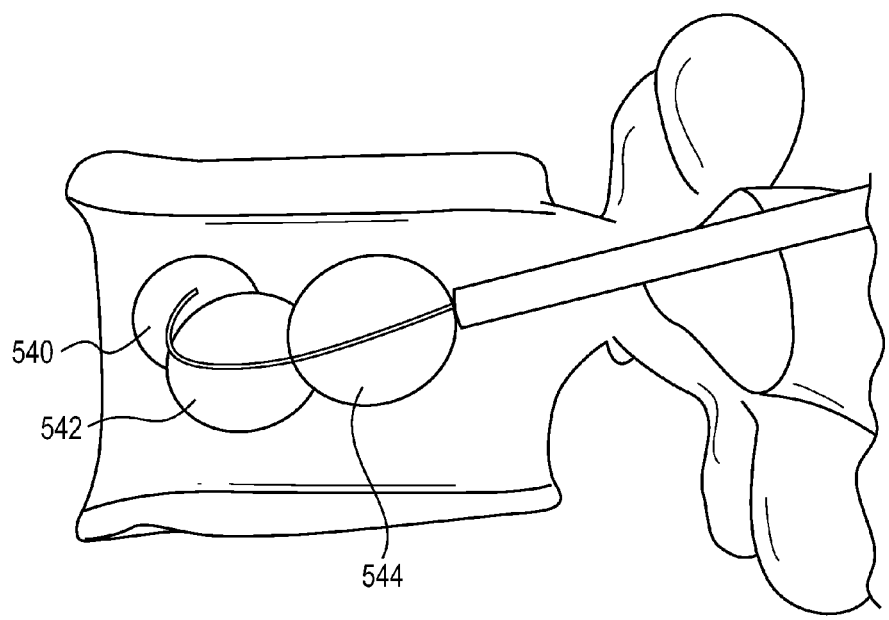
Figure 9:
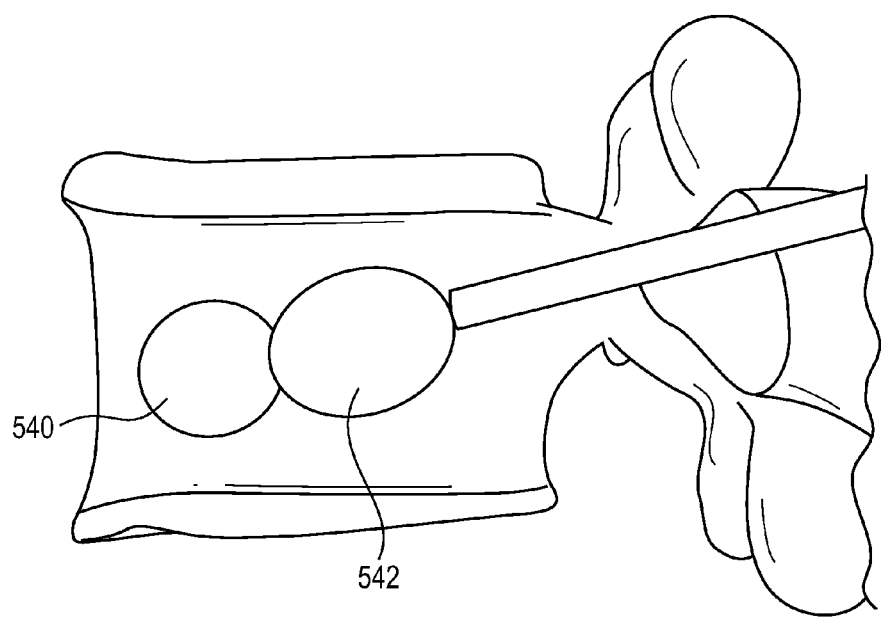
FIG. 9 shows a side view of a two-cavity implementation of the present methods.

The anterior-posterior offset aspect of cavity formation using the present method is illustrated in FIGS. 8-9, which show, respectively, a two-cavity and a three-cavity aspect from a side view perspective. A treating physician can determine the number, orientation (posterior versus inferior, left versus right, and anterior versus posterior), size, and relative overlap—if any—of a plurality of cavities, based upon the bone being targeted and the desire for restoration and/or repair.

Specifically, FIG. 9 shows a side view embodying the described method as having formed two cavities, a first cavity 540 of which is mostly anterior of the second cavity 542. The second cavity overlaps with and is substantially continuous with the first cavity. FIG. 8 shows a side view perspective of first, second, and third cavities 540, 542, 544 shown top-down in FIG. 7. The contour of a solid-body stylet 472 is shown extended through the cavities, with the delivery tube not extended over its length, in order to provide some positional perspective regarding the path of a delivery tube 414 (and/or delivery cannula 470) and balloon during the inflation/deflation/retraction that formed the cavities. As such, it should be appreciated that such a stylet 472 may be used to position the delivery tube 414 for delivering curable material in the manner described above with reference to FIGS. 5C-5D. Alternatively, as discussed above, the stylet may be embodied as a stylet with a lumen (e.g., configured as a pre-curved delivery cannula stylet 470) which can be used for initial cannulation/cavity-formation, withdrawn from the delivery tube 414 to allow operation of a balloon or other expandable member, then reintroduced for use in delivering curable material.

The cavities are offset from each other along each of the anterior-posterior, left-right, and top-bottom axes of the vertebra. This illustration provides one example of how a single access point (e.g., unipedicular approach in a vertebra) may provide for treatment throughout a bone. Specific location of cavities for treatment will, of course, vary based upon assessment of patient need, the type of bone being treated, and other medically relevant indicia.

Those of skill in the art will appreciate that embodiments not expressly illustrated herein may be practiced within the scope of the claims, including that features described herein for different embodiments, and in different claims, may be combined with each other and/or with currently-known or future-developed technologies while remaining within the scope of the claims. This includes providing the apparatus, a kit, and/or instructions (spoken, written, or otherwise) for conducting the inventive methods herein described. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A method for stabilizing a bone structure, the method comprising:
   directing an access cannula, with a longitudinal axis, into a bone structure;
   directing a polymer delivery tube through an access site into the bone structure, where the delivery tube extends through and beyond a distal end of the access cannula to a first target region, forming a tubular cavity along a delivery tube length within the bone structure;
   retracting longitudinally the delivery tube from a distal portion of the tubular cavity;
   directing an expandable member to, and then expanding the expandable member in, the distal portion of the tubular cavity to form a first cavity having a larger diameter than the tubular cavity;
   deflating, then retracting longitudinally the expandable member and the delivery tube to a desired location in the tubular cavity which location is nearer than the location of the first cavity to the access site;
   expanding again the expandable member in the desired location of the tubular cavity, to form a second cavity with a larger diameter than the tubular cavity and disposed between the first cavity and the access site; and
   filling at least a portion of the first cavity and the second cavity with a curable material.

2. The method of claim 1, where the step of directing a delivery tube comprises providing a stylet disposed longitudinally through the delivery tube, where said stylet has either a solid cross-section or an internal delivery lumen dimensioned and oriented for delivering curable material; and
   further comprising steps of
      removing the stylet before the step of directing and expanding the expandable member.

3. The method of claim 1, where the bone structure is selected from a group consisting of a vertebra, a long bone, an irregular bone, or a flat bone.

4. The method of claim 3, where bone structure is a vertebra, and the access cannula is directed through a single pedicle of the vertebra.

5. The method of claim 1, where the second cavity is generally separate and distinct from the first cavity, except for a connecting portion of the tubular cavity.

6. The method of claim 1, where the expandable member includes a fluid-inflatable balloon configured to create a cavity by displacing material adjacent the tubular cavity.

7. The method of claim 1, where the second cavity is substantially continuous with the first cavity.

8. The method of claim 1, further comprising expanding yet again the expandable member in a still less-distal portion of the tubular cavity to form at least a third cavity and filling at least a portion of the at least a third cavity with a curable material.

9. The method of claim 1, where the first cavity and the second cavity are offset relative to each other with respect to a longitudinal axis of the access cannula.

10. The method of claim 1, where the step of filling at least a portion of the first cavity and the second cavity further includes steps of:
   removing the delivery tube;
   directing to the first and/or the second cavity a distal portion of a delivery cannula including an internal delivery lumen dimensioned and oriented for delivering curable material; and
   delivering the curable material via the internal delivery lumen.

11. Providing a kit and instructions for implementing the method of claim 1.

12. A method for stabilizing a bone structure, the method comprising:
   directing an access cannula, with a longitudinal axis, into a bone structure through only a single access point;
   deploying an expandable member through the access cannula into the bone structure;
   expanding, contracting, moving, then re-expanding the expandable member along a track, within the bone structure more than one time to form a plurality of cavities within the bone structure, wherein the track is curved with respect to the longitudinal axis of the access cannula; and
   filling the plurality of cavities at least partially with a curable material via a pre-curved stylet including an internal delivery lumen dimensioned and oriented for delivering curable material.

13. The method of claim 12, where the bone structure is selected from a group consisting of a vertebra, a long bone, an irregular bone, or a flat bone.

14. The method of claim 13, where the single access point is comprised by a pedicle of the vertebra.

15. The method of claim 12, where the plurality of cavities are generally continuous, together forming a larger cavity along the curved track.

16. The method of claim 12, where the plurality of cavities includes three or more cavities.

17. The method of claim 12, wherein:
   the step of deploying an expandable member through the access cannula further comprises providing a delivery tube coaxially disposed through the access cannula with a stylet disposed longitudinally through the delivery tube to form the curved track; and
   the step of deploying the expandable member includes removing the stylet from the delivery tube.

18. The method of claim 12, where the expandable member includes a fluid-inflatable balloon configured to create a cavity by displacing material adjacent the tubular cavity.

19. The method of claim 12, where each cavity of the plurality of cavities is offset relative to other cavities with respect to the longitudinal axis of the access cannula.

20. Providing a kit and instructions for implementing the method of claim 12.

* * * * *